United States Patent
Xu et al.

(10) Patent No.: US 8,192,928 B2
(45) Date of Patent: Jun. 5, 2012

(54) MUTATIONS IN THE MACROPHAGE SCAVENGER RECEPTOR 1 GENE ALTER RISK OF PROSTATE CANCER, ASTHMA, AND CARDIOVASCULAR DISEASE

(75) Inventors: Jianfeng Xu, Clemmons, NC (US); Deborah Meyers, Mocksville, NC (US); Sigun Zheng, Clemmons, NC (US); Patrick C. Walsh, Hunt Valley, MD (US); William B. Isaacs, Glyndon, MD (US); Eugene Bleecker, Winston-Salem, NC (US); David Herrington, Winston Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 295 days.

(21) Appl. No.: 12/504,034

(22) Filed: Jul. 16, 2009

(65) Prior Publication Data
US 2010/0267024 A1   Oct. 21, 2010

Related U.S. Application Data

(63) Continuation of application No. 10/426,262, filed on Apr. 30, 2003, now Pat. No. 7,579,147.

(60) Provisional application No. 60/378,377, filed on May 7, 2002.

(51) Int. Cl.
   *C12Q 1/68* (2006.01)
(52) U.S. Cl. .......................................... 435/6
(58) Field of Classification Search ........................ None
   See application file for complete search history.

(56) References Cited

U.S. PATENT DOCUMENTS

| | | | | |
|---|---|---|---|---|
| 4,302,204 A | 11/1981 | Wahl et al. | ..... | 436/501 |
| 4,358,535 A | 11/1982 | Falkow et al. | ..... | 435/5 |
| 4,563,419 A | 1/1986 | Ranki et al. | ..... | 435/6 |
| 4,683,195 A | 7/1987 | Mullis et al. | ..... | 435/6 |
| 4,683,202 A | 7/1987 | Mullis | ..... | 435/91.2 |
| 4,800,159 A | 1/1989 | Mullis et al. | ..... | 435/91.2 |
| 4,965,188 A | 10/1990 | Mullis et al. | ..... | 435/6 |
| 4,994,373 A | 2/1991 | Stavrianopoulous et al. | ..... | 435/6 |
| 5,767,248 A | 6/1998 | Roses et al. | ..... | 530/388.25 |
| 6,027,896 A | 2/2000 | Roses et al. | ..... | 435/6 |
| 2001/0051344 A1 | 12/2001 | Shalon et al. | | |

FOREIGN PATENT DOCUMENTS
WO   WO 99/52942   10/1999

OTHER PUBLICATIONS

Barnes, Nature Reviews, 2008 3: 183-192.*
Asthma Center Education and Research Fund, disease information, 2011, pp. 1-2.*
Ohar Ja et al. COPD is associated with a macrophage scavenger receptor-1 gene sequence variation. Chest. 2010; 137: 1098-1107.
Kroese M et al. Genetic tests and their evaluation: can we answer the key questions? Genetics in Medicine. Nov./Dec. 2004; 6(6): 475-480.
Lucentini J. Gene association studies typically wrong. The Scientist. Dec. 20, 2004; 18(24): 20.
Hacker UT et al. Lack of association between an interleukin-1 receptor antagonist gene polymorphism and ulcerative colitis. Gut. 1997; 40: 623-627.
Pennisi E. A closer look at SNPs suggests difficulties. Science. Sep. 18, 1998; 281(5384): 1787-1789.
Hope Q et al. Macrophage scavenger receptor 1 999C>T (RS93X) mutation and risk of prostate cancer. Cancer Epidemiology, Biomarkers & Prevention. 2005; 14(2): 397-402.
Seppälä EH et al. Germ-line alterations in MSR1 gene and prostate cancer risk. Clinical Cancer Research. Nov. 1, 2003; 9: 5252-5256.
Lindmark F et al. Analysis of the macrophage scavenger receptor I gene in Swedish hereditary and sporadic prostate cancer. The Prostate. 2004; 59: 132-140.
Linton MF and Fazio S. Class A scavenger receptors, macrophages, and atherosclerosis Current Opinion in Lipidology. Oct. 2001; 12(5): 489-495.
Acton et al. *J Biol. Chem.* 268:3530-3537 (1993).
Bell et al. *J. Neurocytol* 23:605-613 (1994).
Bova et al. *Cancer Res.* 53:3869-3873 (1993).
Carter et al. *Proc. Natl. Acad. Sci* (USA) 89:3367-3371 (1992).
Cui et al. *AJHG* 68:1207-1218 (2001).
DeMarzo et al. *AJP* 155:1985-1992 (1999).
Dhom *J. Cancer Res. Clin. Oncol.* 706:210-218 (1983).
Emi et al. *J. Biol. Chem.* 268(3):2120-2125 (1993).
Fong et al. *J. Biol. Chem.* 274:36808-36816 (1999).
Frank et al. *J. Biol. Chem.* 275:11672-11677 (2000).
Geng et al. *Scand. J. Immunol.* 42:289-296 (1995).
Gibbs et al. *AJHG* 67:100-109 (2000).
Goddard et al. *AJHG* 68:1197-1206 (2001).
Gronberg et al. (1997) *Am. J. Epidemiol.* 146:552-557 (1997).
Heider et al. *FEBS Lett.* 505:185-190 (1999).
Latil et al. *Virchows Arch.* 432:389-406 (1998).
Matsumoto et al. *Proc. Natl. Acad. Sci.* (USA) 87(23):9133-9137 (1990).
Mietus-Snyder et al. *Areterioscler. Thromb. Vasc. Biol.* 18:1440-1449 (1998).
Nakamura et al. *Biochem. Biophys. Res. Commun.* 290:858-864 (2002).
Nelson et al. *Urology* 57:39-45 (2001).
Ostrander et al. *Am. J. Hum. Genet.* 67:1367-1375 (2000).
Platt et al. *J. Clin. Invest.* 108:649-654 (2001).
Schaid et al. *AJHG* 62:1425-1438 (1998).
Shimura et al. *Cancer. Res.* 60:5857-5861 (2000).
Strickler et al. *Epidemiol. Rer.* 23:144-151 (2001).
Suzuki et al. *Nature* 386:292-296 (1997).
Thomas et al. *J. Exp. Med.* 191:147-156 (2000).
Xu et al. *Am. J. Hum. Genet.* 69:341-350 (2001).
Xu et al. *Hu. Genet.* 108:335-345 (2001).
Sun et al. (2006) "Meta-Analysis of Association of Rare Mutations and Common Sequence Variations in the MSR1 Gene and Prostate Cancer Risk" *The Prostate* 66:728-737.
Zeki AA et al. The asthma-COPD overlap syndrome: a common clinical problem in the elderly. Journal of Allergy. vol. 2011, Article ID 861925, 10 pages.

* cited by examiner

*Primary Examiner* — Hong Sang
(74) *Attorney, Agent, or Firm* — Myers Bigel Sibley & Sajovec, P.A.

(57) ABSTRACT

The present invention discloses methods of screening a subject for increased likelihood or risk of certain diseases or disorders. This method comprises detecting the presence or absence of at least one mutation in the MSR1 gene wherein the presence or absence of such mutation indicates an increased risk for certain diseases, such as cancer asthma and/or cardiovascular diseases.

15 Claims, 4 Drawing Sheets

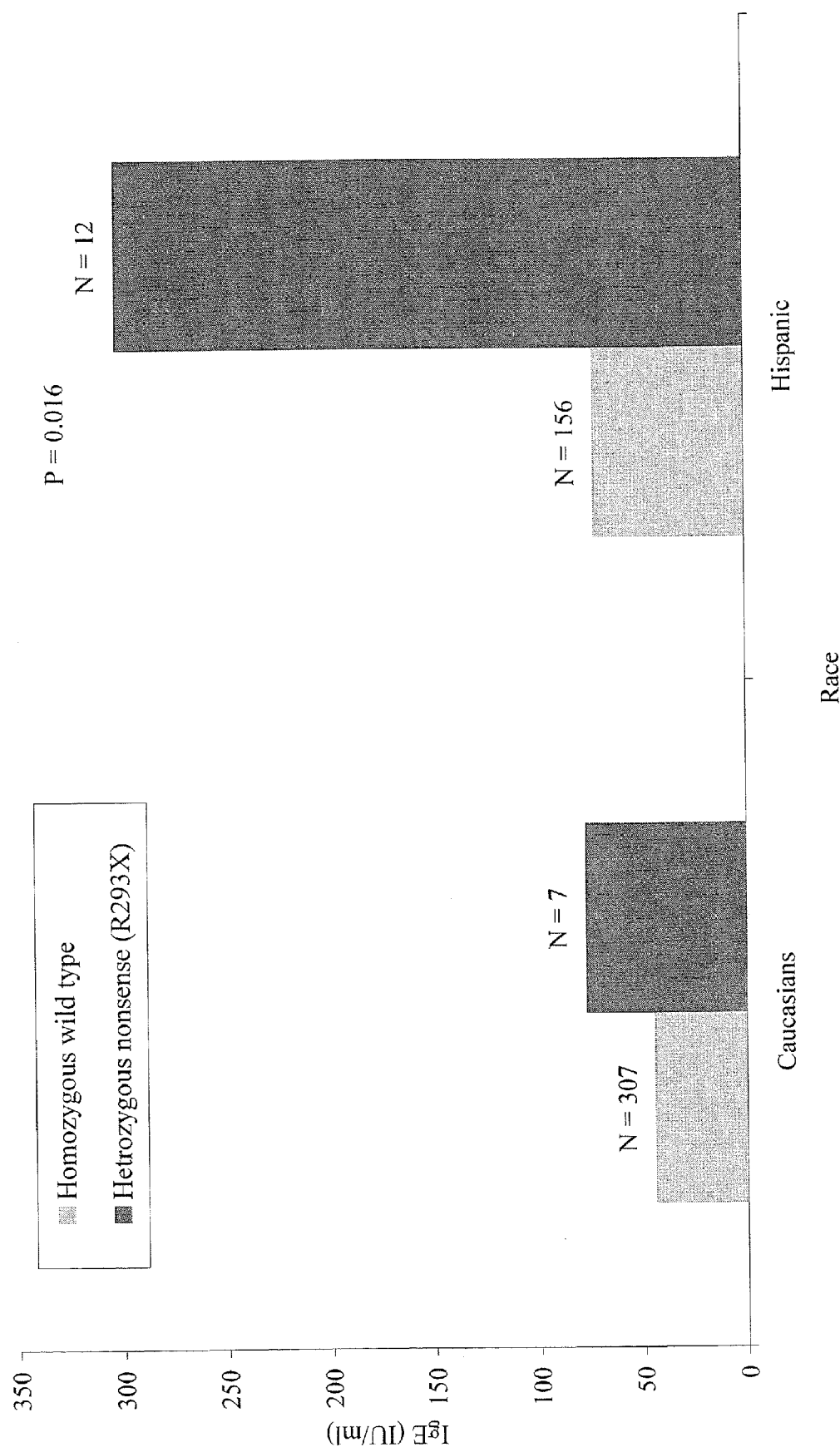

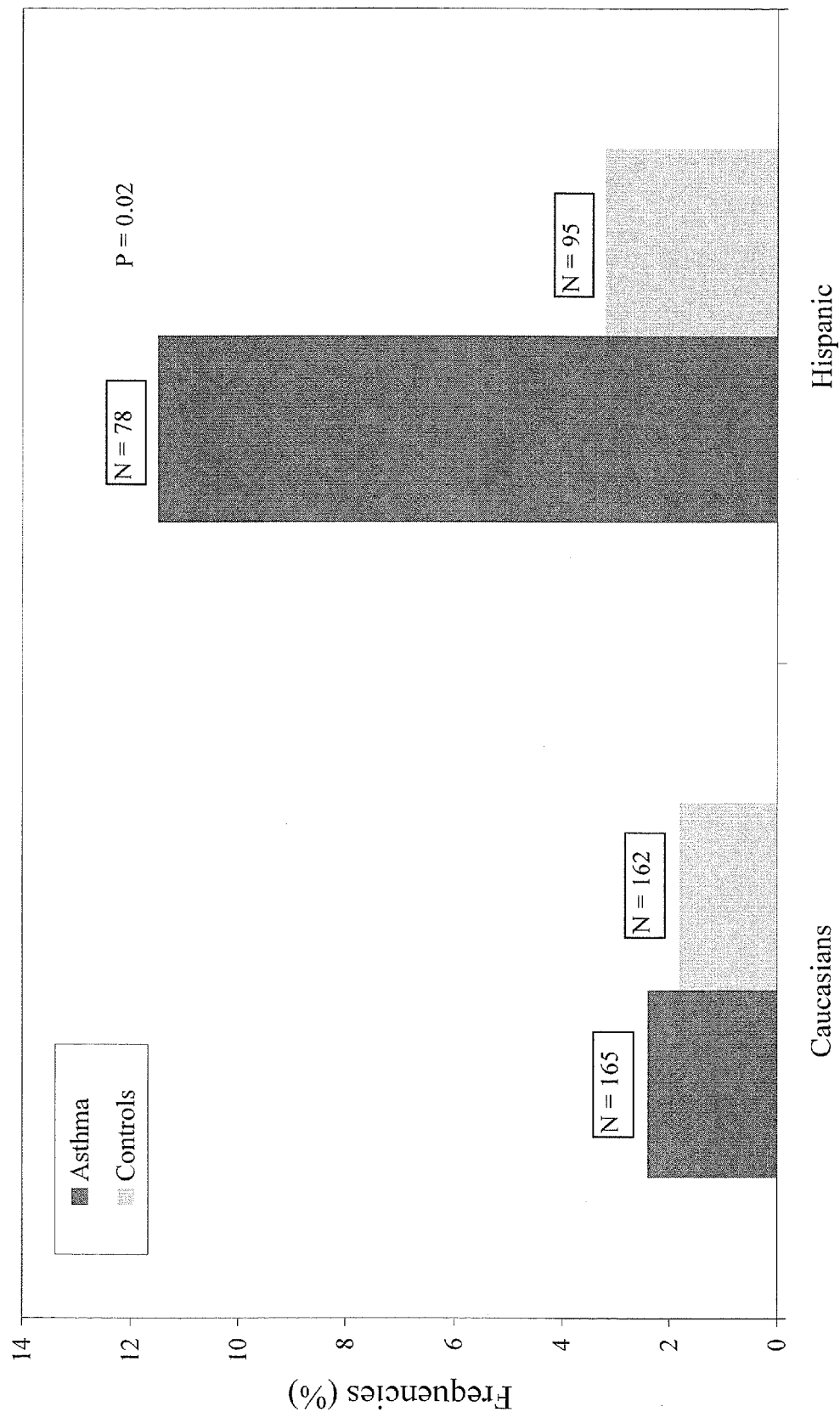

SEQUENCE LISTING

<160> NUMBER OF SEQ ID NOS: 2

<210> SEQ ID NO 1
<211> LENGTH: 2028
<212> TYPE: DNA
<213> ORGANISM: Homo sapiens
<220> FEATURE:
<221> NAME/KEY: CDS
<222> LOCATION: (47)..(1402)

<400> SEQUENCE: 1

```
agagaagtgg ataaatcagt gctgctttct ttaggacgaa agaagt atg gag cag            55
                                                 Met Glu Gln
                                                   1 tgg gat cac ttt cac aat caa cag gag gac act gat agc tgc tcc gaa          103
Trp Asp His Phe His Asn Gln Gln Glu Asp Thr Asp Ser Cys Ser Glu
  5                  10                  15 tct gtg aaa ttt gat gct cgc tca atg aca gct ttg ctt cct ccg aat          151
Ser Val Lys Phe Asp Ala Arg Ser Met Thr Ala Leu Leu Pro Pro Asn
 20                  25                  30                  35 cct aaa aac agc cct tcc ctt caa gag aaa ctg aag tcc ttc aaa gct          199
Pro Lys Asn Ser Pro Ser Leu Gln Glu Lys Leu Lys Ser Phe Lys Ala
                 40                  45                  50 gca ctg att gcc ctt tac ctc ctc gtg ttt gca gtt ctc atc cct ctc          247
Ala Leu Ile Ala Leu Tyr Leu Leu Val Phe Ala Val Leu Ile Pro Leu
             55                  60                  65 att gga ata gtg gca gct caa ctc ctg aag tgg gaa acg aag aat tgc          295
Ile Gly Ile Val Ala Ala Gln Leu Leu Lys Trp Glu Thr Lys Asn Cys
         70                  75                  80 tca gtt agt tca act aat gca aat gat ata act caa agt ctc acg gga          343
Ser Val Ser Ser Thr Asn Ala Asn Asp Ile Thr Gln Ser Leu Thr Gly
     85                  90                  95 aaa gga aat gac agc gaa gag gaa atg aga ttt caa gaa gtc ttt atg          391
Lys Gly Asn Asp Ser Glu Glu Glu Met Arg Phe Gln Glu Val Phe Met
100                 105                 110                 115 gaa cac atg agc aac atg gag aag aga atc cag cat att tta gac atg          439
Glu His Met Ser Asn Met Glu Lys Arg Ile Gln His Ile Leu Asp Met
                120                 125                 130 gaa gcc aac ctc atg gac aca gag cat ttc caa aat ttc agc atg aca          487
Glu Ala Asn Leu Met Asp Thr Glu His Phe Gln Asn Phe Ser Met Thr
            135                 140                 145 act gat caa aga ttt aat gac att ctt ctg cag cta agt acc ttg ttt          535
Thr Asp Gln Arg Phe Asn Asp Ile Leu Leu Gln Leu Ser Thr Leu Phe
        150                 155                 160 tcc tca gtc cag gga cat ggg aat gca ata gat gaa atc tcc aag tcc          583
Ser Ser Val Gln Gly His Gly Asn Ala Ile Asp Glu Ile Ser Lys Ser
    165                 170                 175 tta ata agt ttg aat acc aca ttg ctt gat ttg cag ctc aac ata gaa          631
Leu Ile Ser Leu Asn Thr Thr Leu Leu Asp Leu Gln Leu Asn Ile Glu
180                 185                 190                 195 aat ctg aat ggc aaa atc caa gag aat acc ttc aaa caa caa gag gaa          679
Asn Leu Asn Gly Lys Ile Gln Glu Asn Thr Phe Lys Gln Gln Glu Glu
                200                 205                 210 atc agt aaa tta gag gag cgt gtt tac aat gta tca gca gaa att atg          727
Ile Ser Lys Leu Glu Glu Arg Val Tyr Asn Val Ser Ala Glu Ile Met
            215                 220                 225 gct atg aaa gaa gaa caa gtg cat ttg gaa cag gaa ata aaa gga gaa          775
Ala Met Lys Glu Glu Gln Val His Leu Glu Gln Glu Ile Lys Gly Glu
        230                 235                 240 gtg aaa gta ctg aat aac atc act aat gat ctc aga ctg aaa gat tgg          823
```

```
Val Lys Val Leu Asn Asn Ile Thr Asn Asp Leu Arg Leu Lys Asp Trp
    245                 250                 255 gaa cat tct cag acc ttg aga aat atc act tta att caa ggt cct cct      871
Glu His Ser Gln Thr Leu Arg Asn Ile Thr Leu Ile Gln Gly Pro Pro
260                 265                 270                 275 gga ccc ccg ggt gaa aaa gga gat cga ggt ccc act gga gaa agt ggt      919
Gly Pro Pro Gly Glu Lys Gly Asp Arg Gly Pro Thr Gly Glu Ser Gly
                280                 285                 290 cca cga gga ttt cca ggt cca ata ggt cct ccg ggt ctt aaa ggt gat      967
Pro Arg Gly Phe Pro Gly Pro Ile Gly Pro Pro Gly Leu Lys Gly Asp
                    295                 300                 305 cgg gga gca att ggc ttt cct gga agt cga ggc ctc cca gga tat gcc     1015
Arg Gly Ala Ile Gly Phe Pro Gly Ser Arg Gly Leu Pro Gly Tyr Ala
                310                 315                 320 gga agg cca gga aat tct gga cca aaa ggc cag aaa ggg gaa aag ggg     1063
Gly Arg Pro Gly Asn Ser Gly Pro Lys Gly Gln Lys Gly Glu Lys Gly
325                 330                 335 agt gga aac aca tta act cca ttt acg aaa gtt cga ctg gtc ggt ggg     1111
Ser Gly Asn Thr Leu Thr Pro Phe Thr Lys Val Arg Leu Val Gly Gly
340                 345                 350                 355 agc ggc cct cac gag ggg aga gtg gag ata ctc cac agc ggc cag tgg     1159
Ser Gly Pro His Glu Gly Arg Val Glu Ile Leu His Ser Gly Gln Trp
                360                 365                 370 ggt aca att tgt gac gat cgc tgg gaa gtg cgc gtt gga cag gtc gtc     1207
Gly Thr Ile Cys Asp Asp Arg Trp Glu Val Arg Val Gly Gln Val Val
                    375                 380                 385 tgt agg agc ttg gga tac cca ggt gtt caa gcc gtg cac aag gca gct     1255
Cys Arg Ser Leu Gly Tyr Pro Gly Val Gln Ala Val His Lys Ala Ala
                390                 395                 400 cac ttt gga caa ggt act ggt cca ata tgg ctg aat gaa gtg ttt tgt     1303
His Phe Gly Gln Gly Thr Gly Pro Ile Trp Leu Asn Glu Val Phe Cys
405                 410                 415 ttt ggg aga gaa tca tct att gaa gaa tgt aaa att cgg caa tgg ggg     1351
Phe Gly Arg Glu Ser Ser Ile Glu Glu Cys Lys Ile Arg Gln Trp Gly
420                 425                 430                 435 aca aga gcc tgt tca cat tct gaa gat gct gga gtc act tgc act tta     1399
Thr Arg Ala Cys Ser His Ser Glu Asp Ala Gly Val Thr Cys Thr Leu
                440                 445                 450 taa tgcatcatat tttcattcac aactatgaaa tcgctgctca aaaatgattt          1452
tattaccttg ttcctgtaaa atccatttaa tcaatattta agagattaag aatattgccc   1512
aaataatatt ttagattaca ggattaatat attgaacacc ttcatgctta ctattttatg   1572 tctatatttta aatcatttta acttctatag gtttttaaat ggaattttct aatataatga  1632
cttatatgct gaattgaaca ttttgaagtt tatagcttcc agattacaaa ggccaagggt   1692
aatagaaatg cataccagta attggctcca attcataata tgttcaccag gagattacaa   1752 tttttttgctc ttcttgtctt tgtaatctat ttagttgatt ttaattactt tctgaataac  1812
ggaagggatc agaagatatc ttttgtgcct agattgcaaa atctccaatc cacacatatt   1872
gttttaaaat aagaatgtta tccaactatt aagatatctc aatgtgcaat aacttgtgta   1932
ttagatatca atgttaatga tatgtcttgg ccactatgga ccagggagct tatttttctt   1992
gtcatgtact gacaactgtt taattgaatc atgaag                             2028

<210> SEQ ID NO 2
<211> LENGTH: 451
<212> TYPE: PRT
<213> ORGANISM: Homo sapiens

<400> SEQUENCE: 2
```

```
Met Glu Gln Trp Asp His Phe His Asn Gln Gln Glu Asp Thr Asp Ser
1               5                   10                  15

Cys Ser Glu Ser Val Lys Phe Asp Ala Arg Ser Met Thr Ala Leu Leu
                20                  25                  30

Pro Pro Asn Pro Lys Asn Ser Pro Ser Leu Gln Glu Lys Leu Lys Ser
                35                  40                  45

Phe Lys Ala Ala Leu Ile Ala Leu Tyr Leu Leu Val Phe Ala Val Leu
            50                  55                  60

Ile Pro Leu Ile Gly Ile Val Ala Ala Gln Leu Leu Lys Trp Glu Thr
65                  70                  75                  80

Lys Asn Cys Ser Val Ser Ser Thr Asn Ala Asn Asp Ile Thr Gln Ser
                85                  90                  95

Leu Thr Gly Lys Gly Asn Asp Ser Glu Glu Met Arg Phe Gln Glu
                100                 105                 110

Val Phe Met Glu His Met Ser Asn Met Glu Lys Arg Ile Gln His Ile
                115                 120                 125

Leu Asp Met Glu Ala Asn Leu Met Asp Thr Glu His Phe Gln Asn Phe
            130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
                165                 170                 175

Ser Lys Ser Leu Ile Ser Leu Asn Thr Thr Leu Leu Asp Leu Gln Leu
                180                 185                 190

Asn Ile Glu Asn Leu Asn Gly Lys Ile Gln Glu Asn Thr Phe Lys Gln
            195                 200                 205

Gln Glu Glu Ile Ser Lys Leu Glu Glu Arg Val Tyr Asn Val Ser Ala
            210                 215                 220

Glu Ile Met Ala Met Lys Glu Glu Gln Val His Leu Glu Gln Glu Ile
225                 230                 235                 240

Lys Gly Glu Val Lys Val Leu Asn Asn Ile Thr Asn Asp Leu Arg Leu
                245                 250                 255

Lys Asp Trp Glu His Ser Gln Thr Leu Arg Asn Ile Thr Leu Ile Gln
            260                 265                 270

Gly Pro Pro Gly Pro Pro Gly Glu Lys Gly Asp Arg Gly Pro Thr Gly
                275                 280                 285

Glu Ser Gly Pro Arg Gly Phe Pro Gly Pro Ile Gly Pro Pro Gly Leu
            290                 295                 300

Lys Gly Asp Arg Gly Ala Ile Gly Phe Pro Gly Ser Arg Gly Leu Pro
305                 310                 315                 320

Gly Tyr Ala Gly Arg Pro Gly Asn Ser Gly Pro Lys Gly Gln Lys Gly
                325                 330                 335

Glu Lys Gly Ser Gly Asn Thr Leu Thr Pro Phe Thr Lys Val Arg Leu
            340                 345                 350

Val Gly Gly Ser Gly Pro His Glu Gly Arg Val Glu Ile Leu His Ser
            355                 360                 365

Gly Gln Trp Gly Thr Ile Cys Asp Asp Arg Trp Glu Val Arg Val Gly
            370                 375                 380

Gln Val Val Cys Arg Ser Leu Gly Tyr Pro Gly Val Gln Ala Val His
385                 390                 395                 400

Lys Ala Ala His Phe Gly Gln Gly Thr Gly Pro Ile Trp Leu Asn Glu
            405                 410                 415

Val Phe Cys Phe Gly Arg Glu Ser Ser Ile Glu Glu Cys Lys Ile Arg
```

```
                    420                 425                 430
Gln Trp Gly Thr Arg Ala Cys Ser His Ser Glu Asp Ala Gly Val Thr
        435                 440                 445

Cys Thr Leu
    450
```

MUTATIONS IN THE MACROPHAGE SCAVENGER RECEPTOR 1 GENE ALTER RISK OF PROSTATE CANCER, ASTHMA, AND CARDIOVASCULAR DISEASE

CROSS REFERENCE TO RELATED APPLICATION

The present application claims priority to and is a continuation of U.S. patent application Ser. No. 10/426,262, filed Apr. 30, 2003, now U.S. Pat. No. 7,579,147, which claims the benefit of U.S. Provisional Application No. 60/378,377, filed May 7, 2002, the disclosure of each of which is incorporated herein by reference in its entirety.

STATEMENT OF FEDERAL SUPPORT

This invention was made with government support under PHS SPORE CA58236 and grants from the Department of Defense. The United States government has certain rights to this invention.

FIELD OF THE INVENTION

This invention concerns gene mutations that alter the risk or susceptibility to certain diseases, along with methods of use thereof and materials that may be used in such methods.

BACKGROUND OF THE INVENTION

Intense genetic study of familial prostate cancer has resulted in the identification of numerous putative prostate cancer susceptibility loci and several candidate genes, along with a realization of the extensive genetic and etiologic heterogeneity that characterizes this disease (Ostrander et al. (2000) *Am. J. Hum. Genet.* 67, 1367-1375). A gene or genes on 8p22-23 have been implicated in prostate carcinogenesis by the observation of frequent deletions of this region in prostate cancer cells (Latil & Lidereau. (1998) *Virchows Arch.* 432, 389-406), and by three recent linkage studies in hereditary prostate cancer (HPC) families (Xu et al. (2001) *Am. J. Hum. Genet.* 69, 341-350, Gibbs et al. (2000) *Am. J. Hum. Genet.* 67, 100-109, Goddard et al. (2001) *Am. J. Hum. Genet* 68, 1197-1206). Because it functions in multiple processes proposed to be relevant to prostate carcinogenesis (e.g. inflammation, innate and adaptive immunity, oxidative stress, and apoptosis) (De Marzo et al. (1999) *Am. J. Pathol.* 155, 1985-1992, Nelson et al. (2001) *Urology* 57, 39-45), the MSR1 (macrophage scavenger receptor) gene at 8p22 is a promising candidate gene in this region (Platt & Gordon. (2001) *J. Clin. Invest* 108, 649-654).

SUMMARY OF THE INVENTION

Among other things, here we report the results of multiple genetic analyses that indicate germline variants of MSR1 are associated with prostate cancer risk. In a mutation screen of MSR1 in germline DNA samples from 159 HPC probands, one nonsense (R293X) and seven missense mutations (P36A, S41Y, V113A, D174Y, G369S, H441R and P275A) were identified in 11 families, including four of 14 African American families studied. Additionally, we found a novel missense mutation, 154V, in sporadic cases. A family-based linkage test provided statistical evidence that these mutations co-segregate with prostate cancer (P=0.001); importantly, they were either not observed or observed less frequently in 274 men without prostate cancer and in 518 men who were originally ascertained for a non-prostate related study. Sequence analyses predict that the nonsense change and a number of the missense changes observed may significantly impact the function of the protein, and in some cases may impart dominant negative properties. Additionally, the allele frequencies of five other sequence variants in the coding, promoter, and intronic region of the gene are significantly different between prostate cancer cases and controls (P=0.004). These results provide genetic evidence that MSR1 plays an important role in prostate cancer susceptibility in Caucasians and African Americans, through both rare mutations and more common sequence variants.

Accordingly, a first aspect of the present invention is a method of screening a subject for increased likelihood or risk of certain diseases or disorders. The method comprises detecting the presence or absence of at least one mutation in the MSR1 gene, the presence or absence of such mutation indicating an increased risk of certain diseases.

MSR1 mutations of interest herein include, for example, the H441R mutation, the G369S mutation, the R293X mutation, the P275A mutation, the DF174Y mutation, the V113A mutation, the S41Y mutation, the P36A mutation the 154V mutation, and other mutations which can be determined by skilled persons in light of the information presented herein.

In one embodiment, the presence of an MSR1 mutation as described above indicates an increased risk of asthma in the subject, as compared to subjects without the aforesaid mutation.

In another embodiment, the presence of an MSR1 mutation as described above indicates an increased risk of prostate cancer in said subject, as compared to subjects without the said mutation.

In yet another embodiment, the absence of an MSR1 mutation as described above indicates an increased risk of cardiovascular disease in said subject, as compared to subjects with the said mutation (i.e., the presence of an MSR 1 mutation as described above indicates a decreased risk of cardiovascular disease in said subjects, as compared to subjects without the said mutation).

A further aspect of the present invention is the use of a means of detecting an MSR1 mutation as described herein in determining if a subject is at increased or decreased risk for a disease as described above.

Still further aspects of the present invention include kits, reagents such as oligonucleotide probes, restriction enzymes and other such means for carrying out methods as described above, the use of such reagents for the preparation of kits or diagnostic reagents for carrying out the methods described above, the use of the MSR1 mutations described above in structuring clinical trials of active agents for treating prostate cancer, asthma and/or cardiovascular disease as discussed above, and the use of the MSR1 mutations described herein as targets for rational drug design.

The foregoing and other objects and aspects of the present invention are explained in greater detail in the drawings herein and the specification set forth below.

Figure 1:
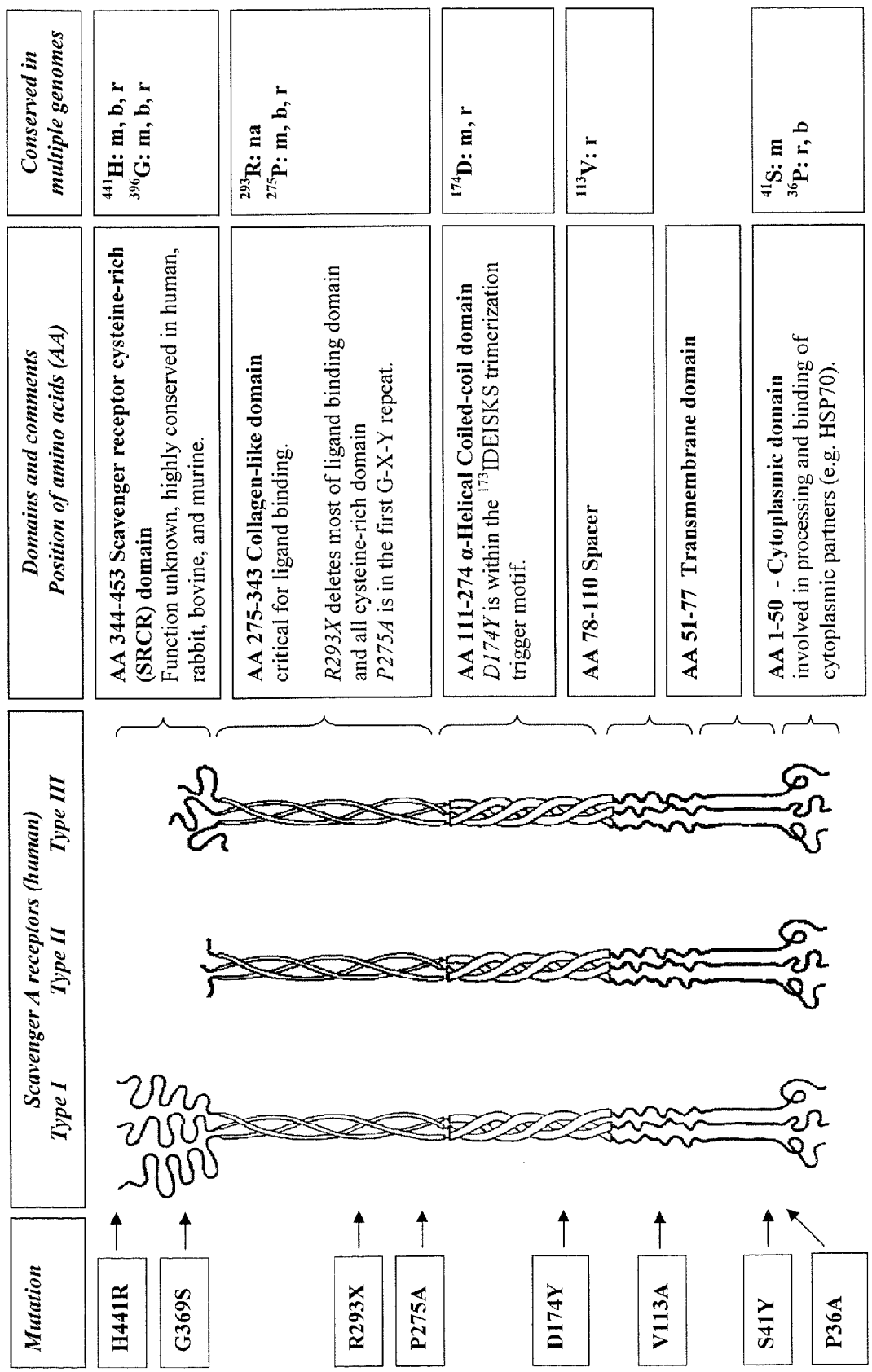
FIG. 1 depicts a schematic of scavenger A receptor, with three isoforms. The predictive functional domains and corresponding position of amino acid, as well as the results from protein alignment of multiple genomes is shown on the right side. The location of the rare mutations identified in the current study on the left side.

FIG. 3 is a bar graph depicting total serum IgE in individuals homozygous for the wild-type MSR1, or heterozygous for the R293X mutation.

FIG. 4 is a bar graph showing the frequency of the MSR1 nonsense mutation R293X in asthma patients as compared to controls.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Subjects for screening and/or treatment with the present invention are, in general, human subjects, including male and female subjects, with male subjects preferred for the purpose of screening for prostate cancer risk. The subject may be of any race and any age, including juvenile, adolescent, and adult, with adult subjects currently preferred. It will be appreciated by those skilled in the art that, while the present methods are useful for screening subjects to provide an initial indication of the suitability of a patient for a particular treatment, this information will typically be considered by a clinician or medical practitioner in light of other factors and experience in reaching a final judgment as to the treatment which any given subject should receive.

Polymorphism detection. In general, the step of detecting the polymorphism of interest may be carried out by collecting a biological sample containing DNA from the subject, and then determining the presence or absence of DNA containing the polymorphism of interest in the biological sample. Any biological sample which contains the DNA of that subject may be employed, including tissue samples and blood samples, with blood cells being a particularly convenient source. The nucleotide sequence of the human MSR1 gene is known and suitable probes, restriction enzyme digestion techniques, or other means of detecting the polymorphism may be implemented based on this known sequence in accordance with standard techniques. See, e.g., U.S. Pat. Nos. 6,027,896 and 5,767,248 to A. Roses et al. (Applicants specifically intend that the disclosures of all United States patent references cited herein be incorporated by reference herein in their entirety).

In describing peptides of this invention, the conventional and non-conventional abbreviations for the various amino acids may be used. They are: Ala=A=Alanine; Val=V=Valine; Leu=L=Leucine; Ile=I=Isoleucine; Pro=P=Proline; Phe=F=Phenylalanine; Trp=W=Tryptophan; Met=M=Methionine; Gly=G=Glycine; Ser=S=Serine; Thr=T=Threonine; Cys=C=Cysteine; Tyr=Y=Tyro sine; Asn=N=Asparagine; Gln=Q=Glutamine; Asp=D=Aspartic Acid; Glu=E=Glutamic Acid; Lys=K=Lysine; Arg=R=Arginine; and His=H=Histidine.

The human macrophage scavenger receptor protein sequence and corresponding nucleotide sequences are known. See, e.g., M. Emi et al., *J. Biol. Chem.* 268 (3), 2120-2125 (1993); A. Matsumoto et al., *Proc. Natl. Acad. Sci. USA* 87(23), 9133-9137 (1990); NCBI Accession Number P21757 (protein) and GenBank Accession Number D90187 (mRNA) (the disclosures of which are to be incorporated herein by reference).

Thus, in one embodiment the amino acid sequence (SEQ ID NO: 2) of a human macrophage scavenger receptor protein I is:

```
  1 meqwdhfhnq qedtdscses vkfdarsmta llppnpknsp slqeklksfk aalialyllv
 61 favlipligi vaaqllkwet kncsvsstna nditqsltgk gndseeemrf qevfmehmsn
121 mekriqhild meanlmdteh fqnfsmttdq rfndillqls tlfssvqghg naideisksl
181 islnttlldl qlnienlngk igentfkqqe eiskleervy nvsaeimamk eeqvhleqei
241 kgevkvinni tndlrlkdwe hsqtlrnitl iqgppgppge kgdrgptges gprgfpgpig
301 ppglkgdrga igfpgsrglp gyagrpgnsg pkgqkgekgs gntltpftkv rlvggsgphe
361 grveilhsgq wgticddrwe vrvgqvvcrs lgypgvqavh kaahfgqgtg piwlnevfcf
421 gressieeck irqwgtracs hsedagvtct l
```

In addition, in one embodiment the cDNA sequence (SEQ ID NO: 1) encoding human macrophage scavenger receptor protein I is as set forth below, with the translated sequence beginning at nucleotide 47:

```
  1 agagaagtgg ataaatcagt gctgctttct ttaggacgaa agaagtatgg agcagtggga
 61 tcactttcac aatcaacagg aggacactga tagctgctcc gaatctgtga aatttgatgc
121 tcgctcaatg acagctttgc ttcctccgaa tcctaaaaac agcccttccc ttcaagagaa
```

```
-continued
 181 actgaagtcc ttcaaagctg cactgattgc cctttacctc ctcgtgtttg cagttctcat 241 ccctctcatt ggaatagtgg cagctcaact cctgaagtgg gaaacgaaga attgctcagt 301 tagttcaact aatgcaaatg atataactca aagtctcacg ggaaaaggaa atgacagcga 361 agaggaaatg agatttcaag aagtctttat ggaacacatg agcaacatgg agaagagaat 421 ccagcatatt ttagacatgg aagccaacct catggacaca gagcatttcc aaaatttcag 481 catgacaact gatcaaagat ttaatgacat tcttctgcag ctaagtacct tgttttcctc 541 agtccaggga catgggaatg caatagatga aatctccaag tccttaataa gtttgaatac 601 cacattgctt gatttgcagc tcaacataga aaatctgaat ggcaaaatcc aagagaatac 661 cttcaaacaa caagaggaaa tcagtaaatt agaggagcgt gtttacaatg tatcagcaga 721 aattatggct atgaaagaag aacaagtgca tttggaacag gaaataaaag gagaagtgaa 781 agtactgaat aacatcacta atgatctcag actgaaagat tgggaacatt ctcagacctt 841 gagaaatatc actttaattc aaggtcctcc tggaccccg ggtgaaaaag gagatcgagg 901 tcccactgga gaaagtggtc cacgaggatt tccaggtcca ataggtcctc cgggtcttaa 961 aggtgatcgg ggagcaattg gctttcctgg aagtcgagga ctcccaggat atgccggaag 1021 gccaggaaat tctggaccaa aaggccagaa aggggaaaag gggagtggaa acacattaac 1081 tccatttacg aaagttcgac tggtcggtgg gagcggccct cacgaggga gagtggagat 1141 actccacagc ggccagtggg gtacaatttg tgacgatcgc tgggaagtgc gcgttggaca 1201 ggtcgtctgt aggagcttgg gatacccagg tgttcaagcc gtgcacaagg cagctcactt 1261 tggacaaggt actggtccaa tatggctgaa tgaagtgttt tgttttggga gagaatcatc 1321 tattgaagaa tgtaaaattc ggcaatgggg gacaagagcc tgttcacatt ctgaagatgc 1381 tggagtcact tgcactttat aatgcatcat attttcattc acaactatga aatcgctgct 1441 caaaaatgat tttattacct tgttcctgta aaatccattt aatcaatatt taagagatta 1501 agaatattgc ccaaataata ttttagatta caggattaat atattgaaca ccttcatgct 1561 tactatttta tgtctatatt taaatcattt taacttctat aggtttttaa atggaattt 1621 ctaatataat gacttatatg ctgaattgaa cattttgaag tttatagctt ccagattaca 1681 aaggccaagg gtaatagaaa tgcataccag taattggctc caattcataa tatgttcacc 1741 aggagattac aattttttgc tcttcttgtc tttgtaatct atttagttga ttttaattac 1801 tttctgaata acggaaggga tcagaagata tcttttgtgc ctagattgca aaatctccaa 1861 tccacacata ttgttttaaa ataagaatgt tatccaacta ttaagatatc tcaatgtgca 1921 ataacttgtg tattagatat caatgttaat gatatgtctt ggccactatg gaccagggag 1981 cttattttc ttgtcatgta ctgacaactg tttaattgaa tcatgaag
```

In describing the mutations disclosed herein in the novel proteins described herein, and the nucleotides encoding the same, the naming method is as follows: [amino acid replaced][amino acid number in sequence of known protein][alternate amino acid]. For example, for the H441R variant disclosed herein, histidine at the 441st amino acid in the protein is replaced with arginine.

The polymorphisms described herein can be detected in accordance with known techniques based upon the known sequence information of the human MSR1 gene and the information provided herein. Novel nucleic acid sequences and proteins described herein can be isolated from human sources based upon the information provided herein or produced by other means such as site-directed mutagenesis of known or available nucleic acids, coupled as necessary with techniques for the production of recombinant proteins known in the art.

Determining the presence or absence of DNA containing a polymorphism or mutation of interest may be carried out with an oligonucleotide probe labeled with a suitable detectable group, or by means of an amplification reaction such as a polymerase chain reaction or ligase chain reaction (the product of which amplification reaction may then be detected with a labeled oligonucleotide probe or a number of other techniques). Further, the detecting step may include the step of detecting whether the subject is heterozygous or homozygous for the polymorphism of interest. Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al. (applicants specifically intend that the disclosures of all U.S. Patent references cited herein be incorporated herein by reference).

Amplification of a selected, or target, nucleic acid sequence may be carried out by any suitable means. See generally D. Kwoh and T. Kwoh, Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "3SR") (see J. Guatelli et al., Proc. Natl. Acad. Sci. USA 87, 1874-1878 (1990)), the QB replicase system (see P. Lizardi et al., Bio-Technology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra).

DNA amplification techniques such as the foregoing can involve the use of a probe, a pair of probes, or two pairs of probes which specifically bind to DNA containing the polymorphism of interest, but do not bind to DNA that does not contain the polymorphism of interest under the same hybridization conditions, and which serve as the primer or primers for the amplification of the DNA or a portion thereof in the amplification reaction. Such probes are sometimes referred to as amplification probes or primers herein.

In general, an oligonucleotide probe which is used to detect DNA containing a polymorphism or mutation of interest is an oligonucleotide probe which binds to DNA encoding that mutation or polymorphism, but does not bind to DNA that does not contain the mutation or polymorphism under the same hybridization conditions. The oligonucleotide probe is labeled with a suitable detectable group, such as those set forth below in connection with antibodies. Such probes are sometimes referred to as detection probes or primers herein.

Probes and primers, including those for either amplification and/or protection, are nucleotides (including naturally occurring nucleotides such as DNA and synthetic and/or modified nucleotides) are any suitable length, but are typically from 5, 6, or 8 nucleotides in length up to 40, 50 or 60 nucleotides in length, or more. Such probes and or primers may be immobilized on or coupled to a solid support such as a bead, chip, pin, or microtiter plate well in accordance with known techniques, and/or coupled to or labeled with a detectable group such as a fluorescent compound, a chemiluminescent compound, a radioactive element, or an enzyme in accordance with known techniques.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. When PCR conditions allow for amplification of all allelic types, the types can be distinguished by hybridization with allelic specific probe, by restriction endonuclease digestion, by electrophoresis on denaturing gradient gels, or other techniques.

Ligase chain reaction (LCR) is also carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

It will be readily appreciated that the detecting steps described herein may be carried out directly or indirectly. For example, a polymorphism or mutation could be detected by measuring by digestion with restriction enzymes, detection of markers that are linked to the mutation or polymorphism, etc.

Kits useful for carrying out the methods of the present invention will, in general, comprise one or more oligonucleotide probes and other reagents for carrying out the methods as described above, such as restriction enzymes, optionally packaged with suitable instructions for carrying out the methods.

The new polymorphisms described herein provide novel nucleic acids encoding the human MSR1, along with probes such as described above that bind selectively thereto. Such nucleic acids can be inserted into vectors such as plasmids, optionally associated with or placed under the control of a promoter, and the nucleic acids may be inserted into host cells and optionally expressed therein (when the promoter is operative in the host cell) to produce MSR1.

The present invention also provides a method of conducting a clinical trial on a plurality of human subjects or patients. Such methods advantageously permit the refinement of the patient population so that advantages of particular treatment regimens (typically administration of pharmaceutically active organic compound active agents) can be more accurately detected, particularly with respect to particular subpopulations of patients. In general, such methods comprise administering a test active agent or therapy to a plurality of subjects (a control or placebo therapy typically being administered to a separate but similarly characterized plurality of subjects) and detecting the presence or absence of at least one mutation or polymorphism as described above in the plurality of subjects. The polymorphisms may be detected before, after, or concurrently with the step of administering the test therapy. The influence of one or more detected polymorphisms or absent polymorphisms on the test therapy can then be determined on any suitable parameter or potential treatment outcome or consequence, including but not limited to: the efficacy of said therapy, lack of side effects of the therapy, etc.

The present invention is explained in greater detail in the following non-limiting examples.

Example 1

Methods

Subjects. Study subjects were from four different populations. The first subjects were 159 HPC families ascertained at the Brady Urology Institute at Johns Hopkins Hospital (Baltimore, Md.), through referrals, review of medical records for patients seen at Johns Hopkins Hospital for treatment of prostate cancer, and respondents to various lay publications describing our studies (Xu et al. (2001) *Hum. Genet.* 108, 335-345). Each family had at least three first-degree relatives affected with prostate cancer. The diagnosis of prostate cancer was then verified by medical records. The mean age at prostate cancer diagnosis for these probands was 61 years; 133 (84%) were Caucasian, and 14 (8.8%) were African American. The second was a case-control population. Two hundred and forty-six sporadic cases were recruited from patients that underwent treatment for prostate cancer at the Johns Hopkins Hospital and did not have first-degree relatives affected with prostate cancer. Among them, 233 are Caucasians and 13 are African Americans. For each subject, the diagnosis of prostate cancer was confirmed by pathology reports. Mean age at diagnosis for these cases was 58.6 years. Two hundred and thirty-nine non-prostate cancer controls were recruited among men participating in screening programs for prostate cancer who had normal digital rectal examination (DRE) and normal PSA levels (i.e., <4 ng/ml), consisting of 164 Caucasians and 75 African Americans. The mean age at examination was 57.5 years. The third group was a small African American case-control population from Wake Forest University School of Medicine. This population was added to this study to enlarge the sample size of African Americans. Among them, 31 were prostate cancer cases and 20 were unaffected controls that participated in screening programs, who were at least 50 years of age and had normal DRE and PSA levels. The last was a subset (n=518) of a large population study of asbestos-exposed workers who were recruited to study the impact of genetic and environmental factors on the development of asbestos-induced lung diseases. Serum PSA levels and prostate cancer diagnoses were later obtained. Participants worked as painters, pipefitters, plumbers, operators, and electricians. A physical examination was performed on all participants. The Institutional Review Boards of Johns Hopkins University, St. Louis University, and Wake Forest University approved each of the study protocols.

Sequencing methods and SNP genotyping. The primers for PCR are available upon request. All PCR reactions were performed in a 10 µl volume consisting of 30 ng genomic DNA, 0.2 µM of each primer, 0.2 mM of each dNTP, 1.5 mM $MgCl_2$, 20 mM Tris-HCl, 50 mM KCl, and 0.5 units Taq polymerase (Life Technologies, Inc.). PCR cycling conditions were as follows: 94° C. for 4 minutes; followed by 30 cycles of 94° C. for 30 seconds, specified annealing temperature for 30 seconds, and 72° C. for 30 seconds; with a final extension of 72° C. for 6 minutes. All PCR products were purified using the QuickStep™ PCR purification Kit (Edge BioSystems, Gaithersburg, Md.) to remove dNTPs and excess primers. All sequencing reactions were performed using dye-terminator chemistry (BigDye, ABI, Foster City, Calif.) and then precipitated using 63+/−5% ethanol. Samples were loaded onto an ABI 3700 DNA Analyzer after adding 8 µl of formamide. SNPs were identified using Sequencher™ software version 4.0.5 (Gene Codes Corporation).

Computational Analysis. Complete human mRNA sequence corresponding to MSR1 Type I and II isoforms was assembled by optimal pairwise alignment of mRNA subsequences using the GCG Bestfit program (Accelrys). Only the coding sequence of Type III was available in GenBank. Exon-intron boundaries in NCBI human genome chromosome 8 sequence were delineated by Smith-Waterman alignment of assembled Type I, II, III mRNA sequences to the human genome sequence using the Swat program (P. Green, unpublished). Secondary structure protein analysis was performed using GCG programs. Transmembrane domain prediction was performed using HMMTOP 2.0 (Tusnady & Simon. (2001) *Bioinformatics.* 17, 849-850) and TMHMM 2.0 (Krogh et al. (2001) *J. Mol. Biol.* 305, 567-580).

Accession Numbers. Nucleotide: D13263 Human MSR1 promoter and exon 1; D90187 Type I mRNA coding sequence; D13264 Type 1 3' UTR sequence; D90188 Type II mRNA coding sequence; D13265 Type II 3' UTR sequence; AF037351 Type III coding sequence. Peptide: BAA14298 MSR1 Type I protein sequence; BAA14299 MSR1 Type II protein sequence; AAC09251 Type III protein sequence. Genomic: NT_015280.5 human genome chromosome 8 sequence contig.

Statistical analysis. Hardy-Weinberg Equilibrium (HWE) tests for all SNPs, and linkage disequilibrium (LD) tests for all pairs of SNPs, were performed using the GDA computer program (Weir. (1996) Genetic Data Analysis II: Methods for Discrete Population Genetic Data. Sinauer, Sunderland, Mass.). Linkage analyses were performed using both parametric and non-mode-of-inheritance methods, implemented by the computer program GENEHUNTER (Kruglyak et al. (1996) *Am. J. Hum. Genet.* 58, 1347-1363). For the parametric analysis, the same autosomal dominant model that was used by Smith et al. (1996) *Science* 274, 1371-1374 was assumed. Linkage in the presence of heterogeneity was assessed by use of Smith's admixture test for heterogeneity (Ott. (1998) Analysis of human genetic linkage (3rd ed). Johns Hopkins Press, Baltimore, Md.). A maximum likelihood approach was used to estimate the proportion of linked families ($\alpha$), by maximizing the admixed LOD score (HLOD). A likelihood ratio test was used to test for different proportion of linked families ($\alpha$'s) between two groups of families, and a $\chi^2=4.6\times(HLOD+HLOD_2-HLOD_{total})$ is calculated which has 1 degree of freedom, where $HLOD_1$, $HLOD_2$, and $HLOD_{total}$ are the HLODs for the two subsets of familie and the whole sample, respectively. For the non-mode-of-inheritance analysis, a statistic 'Z-all' in the program was used (Whittemore & Halpern. (1994) *Biometrics* 50, 109-117). To test for co-segregation between the rare mutations and prostate cancer, we constructed a bi-allelic marker by coding all 7 different rare mutations into one mutation. Family-based linkage and association tests were performed using FBAT software (Lissbrant et al. (2000) *Int. J. Oncol.* 17, 445-451). Utilizing data from nuclear families and sibships, FBAT determines an S statistics from the data, which is the linear combination of offspring genotypes and phenotypes. The distribution of the S statistics is generated by treating the offspring genotype data as random, and conditioning on the phenotypes and parental genotypes. A Z statistics and its corresponding p-value are calculated. The hypotheses of differences in allele frequencies between cases and controls were tested based on the $\chi^2$ of Amitage trend tests (Sasieni. (1997) *Biometrics* 53, 1253-1261, Slager & Schaid. (2001) *Hum. Hered.* 52, 149-153), adjusting for age.

Example 2

Results

The present invention also illustrates evidence for a prostate cancer linkage at 8p22-23 in a study of 159 HPC families, each with at least three affected first-degree relatives (Xu et al. (2001) *Am. J. Hum. Genet.* 69, 341-350). Evidence for linkage at this region was also observed in two other HPC family studies (Gibbs, M. et al. (2000) *Am. J. Hum. Genet.* 67, 100-109, Goddard et al. (2001) *Am. J. Hum. Genet.* 68, 1197-1206). Together with the well-known observations that 8p is the most frequent site of loss of heterozygosity (LOH) in prostate cancer cells (Latil & Lidereau. (1998) *Virchows Arch.* 432, 389-406), these results implicate a prostate cancer susceptibility locus at 8p22-23. To identify prostate cancer susceptibility gene(s), known genes and transcripts in this region are being systemically screened and prioritized by biological relevance.

MSR1 is one of two known genes located in a previously characterized homozygous deletion in a clinical prostate cancer sample (Bova et al. (1993) *Cancer Res.* 53, 3869-3873). The MSR1 protein, a Class A scavenger receptor (SR-A), is a multi-domain trimeric molecule composed of identical protein chains. It has two functional isoforms (Type I and II) and one nonfunctional isoform (III), generated by alternative splicing of a single 11-exon mRNA (Matsumoto et al. (1990) *Proc. Natl. Acad. Sci. U.S.A* 87, 9133-9137, Emi et al. (1993) *J. Biol. Chem.* 268, 2120-2125). This macrophage-specific receptor is capable of binding a highly diverse array of polyanionic ligands, ranging from gram negative and positive bacteria, oxidized LDL, to silica, and correspondingly has been linked to a wide variety of normal and pathologic processes including inflammation, innate and adaptive immunity, oxidative stress, and apoptosis (Platt & Gordon. (2001) *J. Clin. Invest* 108, 649-654). This gene presented an important candidate for analysis because of recent hypotheses concerning the mechanisms of prostate carcinogenesis implicate some or all of these processes and the degree of macrophage infiltration have been associated with prostate cancer prognosis in recent studies (Shimura et al. (2000) *Cancer Res.* 60, 5857-5861, Lissbrant et al. (2000) *Int. J. Oncol.* 17, 445-451).

To evaluate the role of MSR1 in prostate cancer a comprehensive genetic study was performed in a large number of subjects from multiple populations. These analyses consisted of: 1) sequencing the entire coding region of the gene in 159 HPC probands; this analysis resulted in the identification of multiple rare mutations as well as common sequence variants; 2) genotyping the 7 identified mutations in all family members of the 159 HPC families to examine co-segregation between the mutations and prostate cancer; 3) genotyping the 7 mutations in additional 276 sporadic cases and 274 unaffected controls to estimate their frequencies in non-hereditary prostate cancer cases and controls; 4) genotyping the 7 mutations in 518 men who were not ascertained for their prostate cancer status to evaluate the mutation frequencies in the general population; and 5) genotyping the 6 identified, frequently observed sequence variants in the case-control population to test for association with prostate cancer.

Mutations and sequence variants of MSR1 were first screened in the germline DNA samples of one affected individual (proband) from each of the 159 HPC families. The PCR products of all 11 exons, exon-intron junctions, promoter region, 5' and 3' UTRs, were directly sequenced. Eight nonsynonymous changes were identified (Table 1 and FIG. 1), including one nonsense mutation at codon 293 (R293X) and seven missense mutations or sequence variants (P36A, S41Y, V113A, D174Y, P275A, G369S, H441R). Although over 130 and 100 SNPs are listed in NCBI's dbSNP database and Celera's Human RefSNP database, respectively, for the MSR1 gene, none of these reported sequence changes lie in the coding region. Since the sequence variants observed had not been previously reported, a study was performed to investigate the co-segregation of these mutations with prostate cancer. In doing so, all family members with available DNA samples among the 159 HPC families (n=1477, including 653 affected individuals) were directly sequenced for these mutations.

Sequence variant R293X. The nonsense mutation in Exon 6 (R293X) was observed in four different families, all of which are Caucasian (Table 1, for reasons of confidentiality, pedigrees were not drawn). The mutation segregates well, although not completely, with prostate cancer in these nuclear families. Eight of the 9 affected brothers in these families had the mutation. The only affected brother who did not have the mutation (in family 30) was diagnosed with prostate cancer at age 78 years, being screened as a result of his family history, and is still alive, while two of his affected brothers died of prostate cancer. Of the two unaffected brothers from whom blood was available in these families, one carried the mutation; this individual was diagnosed with colon cancer at age 70.

Sequence variant D174Y. The missense change (D174Y) in Exon 4 was observed in four families, all African American (there were 14 African American families in our study). Again, the mutation segregates well, but not completely, with prostate cancer in these families (Table 1). Seven of the 9 affected brothers in these families had the mutation, while one unaffected brother also had the mutation; however, this unaffected brother is under 50 years of age. Family 150 provided particularly strong evidence for co-segregation between the mutation and prostate cancer. All six affected men in the family had the mutation, including four brothers, a half paternal brother and his affected son. The half brother's unaffected son did not have the mutation.

TABLE 1

Description of the 11 families with mutations in MSR1

| Mutation | Family | Race | No. with mutation/total | | probable transmission of mutation** | Additional information |
|---|---|---|---|---|---|---|
| | | | Brothers with HPC | Brothers w/o HPC | | |
| R293X | 30 | Caucasian | 2/3 | 1*/1 | Unknown | *The unaffected brother had colon cancer, three other siblings died of |

TABLE 1-continued

Description of the 11 families with mutations in MSR1

| Mutation | Family | Race | Brothers with HPC | Brothers w/o HPC | probable transmission of mutation** | Additional information |
|---|---|---|---|---|---|---|
| | 91 | Caucasian | 1/1 | 0/0 | Maternal | either prostate, lung, or breast cancer. Mother had breast cancer and father is unaffected. |
| | 133 | Caucasian | 2/2 | 0/0 | Paternal | None of the extended paternal relatives had the mutation. Father had rectal cancer, none of the extended maternal relatives, including 4 unaffecteds had the mutation. |
| | 223 | Caucasian | 3/3 | 0/1 | Maternal | None of the extended paternal relative had the mutation. |
| D174Y | 48 | African Am. | 1/2 | 0/0 | Paternal | Father is an obligate carrier, 7 out of 10 paternal siblings had prostate, lung, ovarian, and colon cancers. |
| | 51 | African Am. | 1/1 | 0/0 | Maternal | Mother is a mutation carrier. |
| | 150 | African Am. | 4/4 | 0/0 | Paternal | Paternal half brother and his affected son had the mutation, the unaffected son did not have the mutation. |
| | 165 | African Am | 1/2 | 1/1 | Unknown | A mutation carrier sister died of breast cancer, the unaffected brother is under 50. |
| P36A | 118 | Caucasian | 3/3 | 0/0 | Unknown | One of the affected brothers and another brother had melanoma. |
| V113A | 118 | Caucasian | 3/3 | 0/0 | Unknown | All three mutation carriers had mutation P36A. |
| S41Y | 51 | African Am | 1/1 | 0/0 | Maternal | The mutation carrier had the mutation D174Y. |
| G369S | 196 | Caucasian | 3/3 | 1/1 | Unknown | The unaffected brother is over 70 years old. |
| 441R | 65 | Caucasian | 4/4 | 1/1 | Maternal | The unaffected brother is under 60 years old, mother had breast cancer, none of the extended paternal relatives had the mutation. |
| Total | | | 29/32 | 4/5 | | |

**Primarily based on the haplotype and mutation carrier status in the paternal or maternal relatives Additional sequence variants. Five additional missense mutations were observed in four independent probands. All 11 affected brothers in these four families had the same mutation found in the corresponding proband, although two unaffected brothers also had mutations (Table 1). Family 118 had two mutations (P36A and V113A); however, it is unclear whether these two mutations are on the same chromosome because all three affected brothers shared both parental chromosomes at this locus. The affected individual in Family 51 also had two mutations (S41Y and D174Y) inherited on the same maternal chromosome. Overall, the combined analyses for these seven mutations demonstrated that 29 out of 32 affected sons in these nuclear families had the mutation present in their family. This observation is of interest considering the complexities of the disease, including the significant degree of locus and allelic heterogeneity, phenocopies, and incomplete penetrance. Seven out of these 11 (64%) families had other types of cancer in their first-degree relatives; this is however not significantly higher than the rate in the remaining families (53%).

To formally test for co-segregation between these mutations and prostate cancer in the 159 HPC families a family-based linkage and association analysis was performed as implemented in FBAT computer program (Laird et al. (2000) *Genet. Epidemiol.* 19 Suppl 1, S36-S42), using the status of mutations as a bi-allelic marker. A higher than expected S test statistic was observed for the combined mutant allele (Z=3.17, P=0.001), providing significant evidence for linkage between these mutations and prostate cancer. This result is consistent with the findings from multiple segregation analyses that a rare but highly penetrant autosomal dominant allele segregates in some prostate cancer families (Carter et al. (1992) *Proc. Natl. Acad. Sci. U.S.A* 89, 3367-3371, Gronberg et al. (1997) *Am. J. Epidemiol.* 146, 552-557, Schaid et al. (1998) *Am. J. Hum. Genet.* 62, 1425-1438, Cui et al. (2001) *Am. J. Hum. Genet.* 68, 1207-1218.

Figure 2:
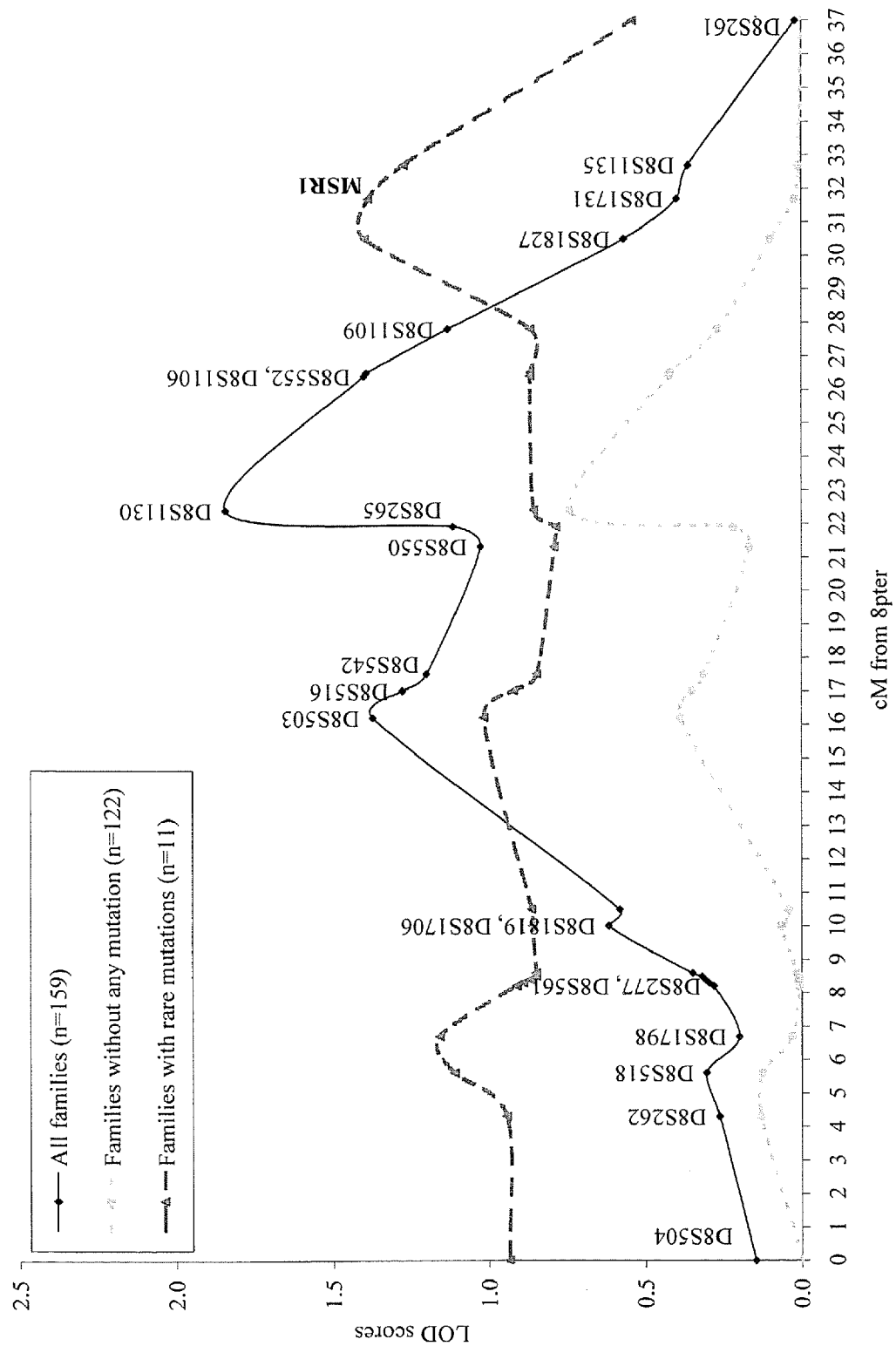
FIG. 2 shows the results of multipoint parametric linkage analyses of prostate cancer susceptibility locus, using 24 markers on chromosome 8p22-23 in the total 159 HPC families, as well as in the subset of 11 families with the rare MSR1 mutations and 122 families without any of the rare mutations nor the frequent sequence variant (P275A).

To examine the relationship between MSR1 mutations and previously observed evidence for linkage of prostate cancer to 8p22-23 (Xu et al. (2001) *Am. J. Hum. Genet.* 69, 341-350) was re-analyzed the linkage data was re-analyzed using the same 24 markers, comparing two sets of families: the 11 families with any of the MSR1 mutations described above and the 122 families without any of these mutations nor the frequent missense mutation P275A (see below). The group of 11 families with mutations provided notably higher LOD scores in this region than the 122 families without mutations (FIG. 2), suggesting that the former families contribute disproportionately to the overall linkage at 8p22-23. More interestingly, the maximum LOD score assuming heterogeneity (HLOD) for these 11 families was 1.40 (P=0.01) at MSR1 region. The proportion of families (a) linked to the locus D8S1135, the closest microsatellite marker to MSR1, was significantly higher in the 11 families (45%) than in the 122 families (2%), with a $\chi_1^2$=4.28 (P=0.038). Six of the 11 mutation carrying families had positive LOD scores at D8S1135, including two families with LOD scores >0.6, and two with LOD >1.0. The remaining five families had negative LOD scores at this locus, possibly due to locus heterogeneity within extended families. For example, in Family 133, while both affected brothers in one sib-ship carry the haplotype bearing the R293X mutation, none of their 11 genotyped maternal relatives in five other branches (including four men affected with prostate cancer) carried this haplotype or the corresponding mutation. Consequently, parametric linkage analysis provided a LOD score of −1.8 for this family. Further examination indicates that the MSR1 mutation in this family was transmitted from the married-in father of the two mutation carriers. This individual did not have prostate cancer; he was diagnosed with rectal cancer before age 60.

To estimate the frequencies of these mutations in non-hereditary prostate cancer patients and unaffected men, additional sporadic prostate cancer patients were screened (233 Caucasians and 43 African Americans) along with unaffected controls (164 Caucasians and 110 African Americans). As shown in Table 2, the mutations P36A and G369S were not found in any Caucasian or African American case-control subjects. The mutation H441R was only found one time, in a Caucasian sporadic prostate cancer cases (0.4%). The mutation S41Y was found one time each in a Caucasian case (0.4%), an African American case (2.3%), and an African American unaffected control (0.9%). This unaffected control carrier has a positive family history of prostate cancer. The other two mutations (R293X and D174Y) were found multiple times in these subjects. The nonsense mutation (R293X) was only found in Caucasian subjects and was more often observed in cases (n=3, 1.3%) than in controls (n=1, 0.6%). This control carrier is 65 years old and has a serum PSA level of 2.1 ng/ml. The missense mutation D174Y was primarily observed in African American subjects and was found more often in cases (n=3, 7.0%) than in unaffected controls (n=2, 1.8%). Both of these unaffected control mutation carriers (ages 56 and 60) have a positive family history of prostate cancer, although their PSA values are normal. The only Caucasian carrier of the mutation D 174Y is a case. Interestingly, all four S41Y mutation carriers (three African American and one Caucasian) also have the mutation D174Y, suggesting a founder effect. Overall, these results suggest that the identified mutations are low frequency and potentially high penetrance. The observation of mutations in some unaffected controls is not surprising considering prostate cancer is a late age of onset disease.

TABLE 2

Summary of the mutations or sequence variants in the coding region of MSR1

| | Number (frequency) of subjects with mutations or sequence variants[1] | | | | | | | |
|---|---|---|---|---|---|---|---|---|
| | P36A | S41Y | V113A | D174Y | P275A | R293X | G369S | H441R |
| Exon | 3 | 3 | 4 | 4 | 6 | 6 | 10 | 11 |
| Nucleotide change | C/G | C/A | T/C | G/T | C/G | C/T | G/A | A/G |
| Caucasians | | | | | | | | |
| HPC families (n = 133) | 1 (0.7%) | 0 (0.0%) | 1 (0.7%) | 0 (0.0%) | 28 (21.0%) | 4 (3.0%) | 1 (0.7%) | 1 (0.7%) |
| HPC probands (n = 133) | 1 (0.7%) | 0 (0.0%) | 1 (0.7%) | 0 (0.0%) | 16 (12.2%) | 2* (1.5%) | 1 (0.7%) | 1 (0.7%) |
| Sporadic cases (n = 233) | 0 (0.0%) | 1 (0.4%) | 2 (0.8%) | 1 (0.4%) | 19 (8.1%) | 3 (1.3%) | 0 (0.0%) | 1 (0.4%) |
| Unaffected controls (n = 164) | 0 (0.0%) | 0 (0.0%) | 1 (0.6%) | 0 (0.0%) | 29 (17.7%) | 1 (0.6%) | 0 (0.0%) | 0 (0.0%) |
| Asbestos exposed men (n = 469) | | | | 0 | | 7** (1.5%) | | |
| African Americans | | | | | | | | |
| HPC families (n = 14) | 0 (0.0%) | 1 (7.1%) | 0 (0.0%) | 4 (28.6%) | 2 (14.3%) | 0 (0.0%) | 0 (0.0%) | 0 (0.0%) |
| HPC probands (n = 14) | 0 (0.0%) | 1 (7.1%) | 0 (0.0%) | 2* (14.3%) | 1 (7.1%) | 0 (0.0%) | 0 (0.0%) | 0 (0.0%) |
| Sporadic cases (n = 43) | 0 (0.0%) | 1 (2.3%) | 0 (0.0%) | 3 (7.0%) | 5 (11.6%) | 0 (0.0%) | 0 (0.0%) | 0 (0.0%) |
| Unaffected controls (n = 110) | 0 (0.0%) | 1 (0.9%) | 0 (0.0%) | 2 (1.8%) | 12 (10.9%) | 0 (0.0%) | 0 (0.0%) | 0 (0.0%) |
| Asbestos exposed men (n = 49) | | | | 2 (4.2%) | | 0 (0.0%) | | |

To begin to understand the frequency and the impact of the mutations R293X and D174Y in the general population 518 men were further screened who were originally ascertained for an asbestos study, regardless of their prostate cancer status. The diagnosis of prostate cancer and serum PSA levels was determined subsequently. The racial distribution of the subjects was 91% Caucasians and 9% African Americans. The mean age of the study subjects at examination was 63.3 years. A diagnosis of prostate cancer was reported by 5.8% (n=30) of men, and this rate was similar in both Caucasians (5.8%, n=27) and African Americans (6.1%, n=3). The nonsense mutation (R293X) was observed 7 times among 469 Caucasians (1.5%) in this group (Table 2). One of these men was among the 27 men subsequently diagnosed with prostate cancer (3.7%). Another nonsense mutation carrier had his prostate removed, and a corresponding undetectable serum PSA level, although his diagnosis of prostate cancer was not confirmed. Two other men had elevated PSA levels (11.8 and 4.2 ng/ml) although they were elderly (ages 72 and 76 years, respectively). No biopsy data were available for these two men. Three other men did not report a diagnosis of prostate cancer and had normal PSA levels (1.5 ng/mL at age 58, 0.8 ng/mL at age 62, and 1.8 ng/mL at age 74). Overall, this mutation was found among 4 of 72 men in this population (5.6%) who have either a diagnosis of prostate cancer or PSA levels outside the normal range ($\geq$4 ng/mL or $\leq$0.2 ng/mL), as compared to 3 of the 397 men (0.7%) without a diagnosis of prostate cancer and normal PSA levels. The difference in mutation carrier rates between these two groups is statistically significant (Fisher Exact Test, P=0.01), suggesting the mutation carriers have an increased risk for prostate pathology (OR=7.72, 95% confidence interval (CI) 1.69-35.2). The missense mutation (D174Y) was observed two times in 49 unaffected African American men (4.1%). One has a PSA of 3.4 ng/mL at age 64 and the other is 43 years of age.

Besides these relatively rare mutations in the coding regions, six other sequence variants were frequently observed in the 159 HPC probands (Table 3), including SNPs in the coding region of Exon 6 (P275A), promoter region (PROd), Intron 5 (15b), and Intron 6 (16a), and an insertion/deletion in Intron 1 (INDEL1), and Intron 7 (INDEL7). Because P275A is an exonic SNP, it was screened among all the family members with available DNA samples in the 159 HPC families. Thirty families had at least one family member who had the variant allele 'G'; of these, 28 are Caucasian families and 2 are African American families. Tests for linkage between this SNP and prostate cancer in these families provided a low LOD score (two-point maximum LOD was 0.27 at $\theta$ of 0.26 using a dominant model) and a low NPL Z-score (0.55, P=0.28). A family-based linkage and association test provided no evidence for linkage, with a lower than expected observed S statistic for the variant allele 'G' (Z=0.12, P=0.90). This data provide scant evidence that this SNP segregates with prostate cancer in these families.

TABLE 3

Sequence variants of MSR1 and their frequencies in cases and controls (Caucasians only)

| SNPs (position)* | Genotype | Genotype frequencies | | | P-values (vs. controls)** | | |
|---|---|---|---|---|---|---|---|
| | | HPC (n = 133) | Sporadic (n = 233) | Controls (n = 164) | HPC | Sporadic | All cases |
| PROd (−14,742 bp) | AA | 0.79 | 0.75 | 0.85 | | | |
| | AG | 0.18 | 0.22 | 0.14 | | | |
| | GG | 0.03 | 0.03 | 0.01 | 0.15 | 0.013 | 0.011 |
| INDEL1 (−14,456 bp) | 11 | 0.78 | 0.75 | 0.85 | | | |
| | 12 | 0.20 | 0.23 | 0.13 | | | |
| | 22 | 0.02 | 0.02 | 0.02 | 0.16 | 0.04 | 0.04 |
| 15b (22,788 bp) | CC | 0.94 | 0.85 | 0.91 | | | |
| | CA | 0.06 | 0.13 | 0.09 | | | |
| | AA | 0 | 0.02 | 0 | 0.46 | 0.04 | 0.19 |
| P275A (22,850 bp) | CC | 0.88 | 0.92 | 0.81 | | | |
| | CG | 0.12 | 0.08 | 0.18 | | | |
| | GG | 0 | 0 | 0.01 | 0.06 | 0.007 | 0.004 |
| 16a (27,565 bp) | CC | 0.95 | 0.92 | 0.96 | | | |
| | CT | 0.05 | 0.08 | 0.04 | | | |
| | TT | 0 | 0 | 0 | 0.48 | 0.2 | 0.24 |
| INDEL7 (34,540 bp) | 11 | 0.87 | 0.89 | 0.78 | | | |
| | 12 | 0.13 | 0.11 | 0.21 | | | |
| | 22 | 0 | 0 | 0.01 | 0.05 | 0.01 | 0.007 |

*Genomic DNA is based on NT_015280 and the position is relative to the ATG site of MSR1
**Based on $\chi^2$ of Amitage trend tests, adjusted for age The SNP P275A and 5 other frequently observed variants were further genotyped in 277 sporadic cases and 271 unaffected controls to assess association between the sequence variants and prostate cancer. Because the majority of case subjects in our study were Caucasians, the statistical test was limited to Caucasians to decrease the impact of potential population stratification. All of the sequence variants were in Hardy-Weinberg Equilibrium among both cases and controls. Four of these sequence variants had significantly different allele frequencies between cases and controls (Table 3). The frequency of the variant allele 'G' of P275A was significantly lower in HPC probands (6%), and in sporadic cases (4%), compared with unaffected controls (10%), suggesting this sequence variant affects prostate cancer susceptibility. However, because the exact function of MSR1, and the impact of the P275A on the MSR1 function are both unknown without further data, it is difficult to classify whether the variant allele protects against or the wild type allele increases risk for prostate cancer. Similar results were observed for INDEL7, 15b, and INDEL1. Because these sequence variants are in strong linkage disequilibrium (P<0.0001 for all pair-wise LD tests), it is difficult to determine whether these sequence variants affect the risk of prostate cancer independently, or through strong linkage disequilibrium with known or unknown variants in the gene. Collectively, the significant association results between these frequently observed SNPs, and the lack of linkage between the SNP P275A and prostate cancer, suggest that these SNPs are prevalent, yet low penetrance sequence variants.

FIG. 3 shows total serum IgE in individuals homozygous for the wild-type MSR1, or heterzygous for the R293X mutation. FIG. 4 shows the frequency of the MSR1 nonsense mutation R293X in asthma patients as compared to controls. There is an increased frequency of the mutation in asthma patients, particularly within the Hispanic population.

Caution should be taken when interpreting and generalizing the findings of the case-control study. As a case-control study, the results are subject to potential population stratification: that is, the different genotype frequencies observed may partially reflect different genetic backgrounds in cases and controls. However, population stratification is unlikely to be substantial in this population because: 1) the statistical tests were limited to Caucasian subjects only, and 2) no evidence was observed for a significant difference in the genetic background between cases and controls, based on a sample of 24 consecutive SNPs recently genotyped on chromosomes 1, 8, 11, 12, and X (data not shown).

The spectrum of coding sequence changes observed in the prostate cancer patients deserves comment. The MSR1 protein has six predicted protein domains, including an amino terminal cytoplasmic domain, transmembrane, spacer, alpha helical coiled coil, collagen-like, and a cysteine rich C-terminal domain (FIG. 1). These protein domains include 1) amino acids 344-453 are the scavenger receptor cysteine-rich (SRCR) domain; 2) amino acids 275-343 are the collagen-like domain; 3) amino acids 111-274 are the α-helical coiled-coil domain; 4) amino acids 78-110 are the spacer; 5) amino acids 51-77 are the transmembrane domain; and 6) amino acids 1-50 are the cytoplasmic domain. The core of the ligand-binding region is located in the lysine rich C-terminal end of the collagen-like domain. The truncating mutation, R293X, results in deletion of most of the collagen-like domain, including the ligand-binding region and the entire cysteine rich domain. Interestingly, (Acton et al. (1993) *J. Biol. Chem.* 268, 3530-3537) demonstrated that the experimentally created MSR1 mutant V296X, is synthesized and processed normally, appearing on the surface of transfected COS cells; however, the protein does not bind typical MSR1 ligands, and most importantly, has the ability to block ligand binding when expressed in the presence of wild type protein, suggesting a dominant negative phenotype. In the helical coiled coil domain of MSR1, mutagenesis studies have defined a critical heptapeptide sequence, $^{173}$IDEISKS, as comprising the functional "trigger", required for proper polymerization of the three MSR1 polypeptide chains (Frank et al. (2000) *J. Biol. Chem.* 275, 11672-11677). Within this sequence, a salt bridge formed between the $^{174}$D and $^{178}$K is thought to be crucial to the activity of the $^{173}$IDEISKS motif. The mutation observed in four African American families, replacing this $^{174}$D with a $^{174}$Y, might interfere with this activity, leading to less efficient trimerization of MSR polypeptides. Substitutions of amino acid residues in the N-terminal cytoplasmic domain of MSR1 have been associated with impaired receptor internalization and decreased ligand processing (Heider et al. (2001) *FEBS Lett.* 505, 185-190, Fong & Le. (1999) *J. Biol. Chem.* 274, 36808-36816). More recently, this domain has been shown to specifically bind multiple cytoplasmic proteins including HSP70, HSP90 and GAPDH (Nakamura et al. (2002) *Biochem. Biophys. Res. Commun.* 290, 858-864), although the critical residues in these interactions have not been mapped. Two missense mutations were found in prostate cancer families in the highly conserved C-terminal cysteine rich domain. Scavenger receptor cysteine-rich (SRCR) domains are the eponymous subunit of the SRCR superfamily, which includes Type A and B domains. Despite being widely found in cell surface molecules and in secreted proteins, their biological functions are not well understood, and ligand-binding properties remain mostly speculative. The loss of SRCR domain in MSR1 isoform II is not detrimental to ligand binding efficiency, although partial loss of the domain in the type III isoform leads to ER membrane entrapment and loss of cell surface activity (Platt & Gordon. (2001) *J. Clin. Invest* 108, 649-654.).

The recurring P275A variant, seen in 30 HPC families, is located in the first G-X-Y repeat of the collagen-like domain (GP$^{275}$P), and this position is conserved in all four mammalian species sequenced to date (man, mouse, cow, and rabbit). Since this sequence variant is common in the general population, and appears to be less common in prostate cancer cases, it will be of considerable interest to see if this mutation has any effect on MSR1 function, and whether it may in fact have some stabilizing influence.

At present it is unknown how a lack of fully functional copies of MSR1 might contribute to prostate carcinogenesis. Expression of MSR1 is largely restricted to macrophages, although expression has also been reported in specialized endothelium, smooth muscle cells, and microglial cells, particularly in response to injury (Geng & Hansson. (1995) *Scand. J. Immunol.* 42, 289-296, Bell et al. (1994) *J. Neurocytol.* 23, 605-613). Several recent studies have examined the correlation between the extent of macrophage infiltration into tumor tissue and prostate cancer outcome (Shimura et al. (2000) *Cancer Res.* 60, 5857-5861, Lissbrant et al. (2000) *Int. J. Oncol.* 17, 445-451). Using immunochemical techniques it has been demonstrated that macrophages present in both benign and cancerous prostate tissues routinely express MSR1 (CME and WBI unpublished observations). DeMarzo et al. and Nelson et al. have obtained data that indicate that inflammation and features associated with this process (proliferative regeneration of prostate epithelium in the presence of increased oxidative stress) most likely play key roles in prostate cancer formation (De Marzo et al. (1999) *Am. J. Pathol.* 155, 1985-1992, Nelson et al. (2001) *Urology* 57, 39-45). MSR1, by virtue of its induction by oxidative stress (Mietus-Snyder et al. (1998) *Arterioscler. Thromb. Vase. Biol.* 18, 1440-1449), and its ability to bind oxidized LDL, may modify levels of reactive oxygen in this context. The finding that MSR1 knockout mice have a reduced capacity to effectively eradicate certain pathogens may also be relevant (Suzuki et al. (1997) *Nature* 386, 292-296, Thomas et al. (2000) *J. Exp. Med.* 191, 147-156.), as an infectious etiology of prostate cancer has long been proposed (Strickler & Goedert. (2001) *Epidemiol. Rev.* 23, 144-151). Finally, the finding that most men over age 70 have lesions histologically identifiable as prostate cancer indicates that the initiation of the disease is quite ubiquitous (Dhom. (1983) *J. Cancer Res. Clin. Oncol.* 106, 210-218), and suggests that inherited influences which increase the rate of progression of these initiated lesions to clinically detectable disease may result in familial clustering of prostate cancer—whether MSR1 mutations play a role in this progressive phase of the disease may be worth investigating.

Thus, the identification of multiple mutations and sequence variants in the MSR1 gene, the co-segregation of multiple mutations with prostate cancer in HPC families, the rarity of these mutations in the general population, and the significant difference in the frequencies of multiple sequence variants between prostate cancer cases and controls, have provided novel genetic evidence that MSR1 may play an important role in both sporadic and hereditary prostate cancer susceptibility.

The foregoing is illustrative of the present invention, and is not to be construed as limiting thereof. The invention is defined by the following claims, with equivalents of the claims to be included therein.

That which is claimed is:

1. A method of screening a subject for increased risk of asthma, comprising:
    detecting the presence or absence of an MSR1 mutation in said subject; and then
    determining that said subject is at increased risk of asthma due to the presence of said MSR1 mutation;
    said MSR1 mutation selected from the group consisting of the R293X mutation, and the P275A mutation.

2. The method of claim 1, wherein said detecting step is carried out by collecting a biological sample from said subject, and detecting the presence or absence of said mutation in said biological sample.

3. The method of claim 1, wherein said detecting step includes a nucleic acid amplification step.

4. The method of claim 1, wherein said detecting step includes a probe hybridization step.

5. The method of claim 1, wherein said detecting step further comprises detecting whether said subject is homozygous for said MSR1 mutation.

6. A method of screening a subject for increased risk of asthma, comprising:
    detecting the presence or absence of an R293X MSR1 mutation in said subject; and then
    determining that said subject is at increased risk of asthma due to the presence of said R293X MSR1 mutation.

7. The method of claim 6, wherein said detecting step is carried out by collecting a biological sample from said subject, and detecting the presence or absence of said R293X MSR1 mutation in said biological sample.

8. The method of claim 6, wherein said detecting step includes a nucleic acid amplification step.

9. The method of claim 6, wherein said detecting step includes a probe hybridization step.

10. The method of claim 6, wherein said detecting step further comprises detecting whether said subject is homozygous for said R293X MSR1 mutation.

11. A method of screening a subject for increased risk of asthma, comprising:
    detecting the presence or absence of a P275A MSR1 mutation in said subject; and then
    determining that said subject is at increased risk of asthma due to the presence of said P275A MSR1 mutation.

12. The method of claim 11, wherein said detecting step is carried out by collecting a biological sample from said subject, and detecting the presence or absence of said P275A MSR1 mutation in said biological sample.

13. The method of claim 11, wherein said detecting step includes a nucleic acid amplification step.

14. The method of claim 11, wherein said detecting step includes a probe hybridization step.

15. The method of claim 11, wherein said detecting step further comprises detecting whether said subject is homozygous for said P275A MSR1 mutation.

* * * * *